(12) United States Patent
Korin

(10) Patent No.: US 6,773,610 B2
(45) Date of Patent: Aug. 10, 2004

(54) METHOD FOR CONTROLLING BIOFILM

(76) Inventor: Amos Korin, 16 Mountainview Dr., Weston, CT (US) 06883

( * ) Notice: Subject to any disclaimer, the term of this patent is extended or adjusted under 35 U.S.C. 154(b) by 62 days.

(21) Appl. No.: 10/215,911

(22) Filed: Aug. 9, 2002

(65) Prior Publication Data
US 2003/0052064 A1 Mar. 20, 2003

Related U.S. Application Data

(62) Division of application No. 09/636,752, filed on Aug. 11, 2000, now Pat. No. 6,464,868.
(60) Provisional application No. 60/153,881, filed on Sep. 14, 1999.

(51) Int. Cl.⁷ .................................................. C02F 1/78
(52) U.S. Cl. ...................... 210/748; 210/760; 210/764; 422/24; 422/28; 134/22.12; 261/DIG. 42; 96/226
(58) Field of Search ....................... 422/24, 28, 186.07, 422/186.1, 186.3, 292, 305; 210/748, 760, 764, 192, 205, 198.1; 134/22.12, 95.1, 166 C; 250/432 R, 436; 261/DIG. 42; 96/226

(56) References Cited

U.S. PATENT DOCUMENTS

| | | | | |
|---|---|---|---|---|
| 3,659,096 A | * | 4/1972 | Kompanek ................. 210/764 |
| 4,767,528 A | * | 8/1988 | Sasaki et al. ................ 210/205 |
| 5,087,198 A | | 2/1992 | Castellini ..................... 433/80 |
| 5,087,419 A | | 2/1992 | Lutz ............................. 422/28 |
| 5,158,454 A | | 10/1992 | Viebahn et al. .............. 433/82 |
| 5,199,604 A | | 4/1993 | Palmer et al. ................ 222/25 |
| 5,308,579 A | | 5/1994 | Melon et al. ................. 422/28 |
| 5,318,443 A | | 6/1994 | Overmyer ................... 433/104 |
| 5,431,861 A | * | 7/1995 | Nagahiro et al. .... 261/DIG. 42 |
| 5,494,576 A | * | 2/1996 | Hoppe et al. ............ 210/198.1 |
| 5,526,841 A | | 6/1996 | Detsch et al. ................. 137/15 |
| 5,527,465 A | | 6/1996 | Dickerson ................... 210/620 |
| 5,529,689 A | | 6/1996 | Korin .......................... 210/232 |
| 5,540,848 A | * | 7/1996 | Engelhard ................... 210/748 |
| 5,573,666 A | | 11/1996 | Korin .......................... 210/232 |
| 5,603,228 A | | 2/1997 | Barthold et al. .............. 62/303 |
| 5,709,546 A | | 1/1998 | Waggoner ..................... 433/82 |
| 5,785,523 A | | 7/1998 | Overmyer ..................... 433/82 |
| 5,795,371 A | | 8/1998 | Ezio ............................ 96/175 |
| 5,807,521 A | | 9/1998 | Franetzki ..................... 422/20 |
| 5,824,243 A | | 10/1998 | Contreras .................. 261/36.1 |
| 5,837,204 A | | 11/1998 | Prevost et al. .............. 422/105 |
| 5,919,417 A | * | 7/1999 | Rutland ........................ 422/28 |
| 5,925,257 A | | 7/1999 | Albelda et al. ............. 210/748 |
| 5,935,431 A | | 8/1999 | Korin .......................... 210/205 |
| 5,942,125 A | | 8/1999 | Engelhard et al. .......... 210/748 |
| 5,942,480 A | | 8/1999 | Prevost et al. .............. 510/161 |
| 5,951,921 A | | 9/1999 | Koganezawa et al. ..... 261/36.1 |
| 5,951,957 A | | 9/1999 | Simpson ..................... 423/219 |
| 5,971,368 A | * | 10/1999 | Nelson et al. ........ 261/DIG. 42 |
| 5,971,371 A | | 10/1999 | Cheng ........................ 261/106 |

(List continued on next page.)

OTHER PUBLICATIONS

Abstract of Publication No. JP401181869A, published on Jul. 19, 1989.
Abstract of Publication No. WO99/65533A.

Primary Examiner—Frank M. Lawrence
(74) Attorney, Agent, or Firm—Ohlandt, Greeley, Ruggiero & Perle, LLP

(57) ABSTRACT

A method for removing biofilm from, and/or for preventing biofilm from forming on, an interior surface of a conduit that receives a supply of water, is performed by disabling the supply of water to the conduit, and passing an ozone-containing gas to the conduit. The ozone-containing gas can be generated from an oxygen-containing gas that is exposed to either a corona discharge or ultraviolet radiation. In an alternate embodiment, the water is disinfected by the ultraviolet radiation. The invention is especially suited for use with dental equipment.

16 Claims, 13 Drawing Sheets

U.S. PATENT DOCUMENTS

| | | | |
|---|---|---|---|
| 5,989,407 A | 11/1999 | Andrews et al. | 205/626 |
| 5,997,702 A | 12/1999 | Koganezawa et al. | 204/266 |
| 5,997,752 A | 12/1999 | Leu et al. | 210/760 |
| 6,001,247 A | 12/1999 | Schulz | 210/192 |
| 6,004,438 A | 12/1999 | Woodson | 204/242 |
| 6,019,117 A | 2/2000 | Detsch et al. | 137/15 |
| 6,019,950 A | 2/2000 | Lai | 422/186.12 |
| 6,024,882 A | 2/2000 | McNeilly et al. | 210/759 |
| 6,027,572 A | 2/2000 | Labib et al. | 134/8 |
| 6,027,642 A | 2/2000 | Prince et al. | 210/180 |
| 6,027,701 A | 2/2000 | Ishioka et al. | 422/186.19 |
| 6,030,526 A | 2/2000 | Porter | 219/198.1 |
| 6,030,586 A | 2/2000 | Kuan | 422/186.07 |
| 6,039,816 A | 3/2000 | Morita et al. | 134/19 |
| 6,054,102 A | 4/2000 | Tanimura et al. | 422/186.15 |
| 6,059,980 A | 5/2000 | Leeming et al. | 210/755 |
| 6,068,778 A | 5/2000 | Steiner et al. | 210/760 |
| 6,267,895 B1 * | 7/2001 | Engelhard et al. | 210/748 |
| 6,482,370 B2 * | 11/2002 | Holsclaw et al. | 422/186.12 |

* cited by examiner

METHOD FOR CONTROLLING BIOFILM

This is a divisional application of Ser. No. 09/636,752, filed on Aug. 11, 2000, now U.S. Pat. No. 6,464,868, and claims priority to provisional application Ser. No. 60/153,881, filed Sep. 14, 1999.

BACKGROUND OF THE INVENTION

1. Field of the Invention

The present invention relates to the control of biofilm and, more particularly, to a method and system for removing biofilm from, and/or for preventing biofilm from forming on, an interior surface of a conduit. The invention is especially suited for use with dental equipment.

2. Description of the Prior Art

As environmental agencies become more aware of the potential health risks associated with drinking either municipal or well water, there has been an ever increasing need for water purification systems that are capable of removing organics, inorganics, particulate, microorganisms, bacteria and viruses from the water supply prior to consumption. Most conventional systems require a series of filtration and chlorination units to properly remove such matters from the water.

Filtration media has been used for years to remove particulate from the water supply, while carbon block filters have been effective in removal of organics and inorganics. However, conventional filters are incapable of removing microorganisms such as bacteria, viruses, yeasts or molds. Ultraviolet radiation in the 200–300 nanometer (nm) range has been extremely effective in killing such microorganisms. As such, germicidal lamps have been used extensively in air and water purification, sewage treatment, protection of food and beverages, and other disinfection and sterilization applications.

Water purification systems that combine the disinfection and sterilization capabilities of ultraviolet radiation with the particulate, organic and inorganic filtering capabilities of conventional filter media are known. Such combined systems provide extremely pure and sterilized drinking water regardless of the origin of the water source.

Even when such water purification systems are used, however, it has been found that bacteria remains in the water and microbial biofilms can form in pipes downstream of the system. Biofilms are formed when bacteria adhere to a hard surface in an aqueous environment. Over a period of time, microbes, entering the pipe stick to an already existing bacterial layer thereby forming a microbial matrix. This matrix, once established, supplies nutrients required for growing additional microbial mass. The formation of biofilms is most pronounced in pipes formed of organic substances such as plastic and rubber, and in pipes having narrow inside diameters.

Although biofilm formation is encountered in most piping systems, the problem is particularly acute in dental unit water lines, as such water lines are usually formed of small diameter plastic tubing. Further, because the water is used in dental work, the prevention of the colonization of the dental unit water lines with bacteria is of particular importance. Nonetheless, biofilm growth has been observed inside new dental unit plastic water lines in as little as two weeks.

These biofilms, when viewed through a scanning electron microscope were found to be characterized by microorganisms embedded in an amorphous matrix of polysaccharides and glycoproteins. The observed amorphous matrix was about 30 to 50 microns thick and capable of shedding bacteria (normal size of about 1 micron) into the water supply. *Pseudomonas aeruginosa* biofilm quantified by measuring distributions of thickness in biofilm samples demonstrated a mean of 33 microns (range of 13.3 microns to 60.0 microns). Most biomass tend to detach in the form of multicellular particles with some particles exceeding 100 microns in size.

Large numbers of Gram-negative bacilli are commonly found to be present in the water outflow/effluent of dental units. The bacteria, which are not easily flushed out, proliferate and produce a matrix, which in turn allows the establishment of other species of bacteria. The biofilm becomes populated with a greater and greater variety of bacteria. It also protects the bacteria during their growth by retaining nutritional material and by allowing a higher level of metabolic activity, all the while protecting the bacteria from biocidal substances. The biofilm gradually becomes visible to the naked eye and can eventually partially obstruct a lumen of a water line.

Although some organisms enter a system as occasional contaminants of a main water supply, the high counts observed are due to colonization and growth on the walls of the small bore plastic tubing of the dental unit water lines.

The conventional method of eliminating biofilm in a dental unit is to fill the water lines with a disinfectant at the end of each day, allowing overnight treatment of the water lines. At the beginning of the next day, the disinfectant is drained, and water flows through cleaned water lines. This avoids contact of the disinfectant with a patient and allows a regular water supply to be used with the dental unit. However, the use of disinfectants is costly and time consuming. Also, there is a potential risk that a portion of the disinfectant will not be removed from the water lines, and will be transported to a dental handpiece and into the patient's mouth.

U.S. Pat. No. 5,785,523 to Overmyer, entitled Dental Water Line Flushing And Disinfecting System, describes a system in which a pressurized disinfectant solution can be selectively delivered along with, or instead of water, to a dental unit. Pressurized air is directed through the water line and the dental unit to expel water. Thereafter, the pressurized disinfectant solution is introduced and preferably left in dental unit overnight. Before reuse of the dental unit, pressurized air must be directed through the system to expel the disinfectant solution.

Chlorine is the most widely used disinfectant for killing microorganisms in water and preventing the formation of biofilms. However, disinfection treatments with chlorine can produce a wide variety of by-products, many of which have been shown to cause cancer and other toxic effects.

Ozone, which is an extremely strong oxidant, is one of the most powerful water sanitizers readily available. Ozone deactivates bacteria and viruses 3125 times faster than chlorine. The prior art teaches the treatment of water with ultraviolet radiation and subsequent treatment with ozone. This prior art further teaches the use of the ultraviolet radiation source as a means for generating the ozone. Some of these prior art units have also used the ultraviolet light source to simultaneously radiate the water, and supply a source of ozone that is then entrained in the water feedstream. Introducing ozone into dental water presents a technical complexity that requires the use of an elaborate apparatus. See, for example, U.S. Pat. No. 5,935,431 to Korin, and U.S. Pat. No. 5,942,125 to Engelhard et al. Disadvantageously, ozonated water has a bitter taste, is toxic, and interferes with the curing of dental work.

There is a need for a method and system for controlling biofilm in a water line in a convenient and time-efficient manner.

There is also a need for such a method and system that minimizes the risk that a user of the water line will be exposed to a residual disinfectant.

SUMMARY OF THE INVENTION

In accordance with the present invention, a method is provided for removing biofilm from, and/or for preventing biofilm from forming on, an interior surface of a conduit that receives a supply of water. The method comprises disabling the supply of water to the conduit, and passing an ozone-containing gas to the conduit.

In accordance with one embodiment of the present invention, a system is provided for removing biofilm from, and/or for preventing biofilm from forming on, an interior surface of a conduit. The system comprises a device for disabling the supply of water to the conduit, and a device for passing an ozone-containing gas through the conduit.

In accordance with another embodiment of the present invention, a system is provided for providing disinfected water to a conduit, and for removing biofilm from, and/or for preventing biofilm from forming on, an interior surface of a conduit. The system comprises an ultraviolet lamp disposed within an ultraviolet radiation permeable sleeve such that a channel is formed between an outer surface of the ultraviolet lamp and an inner surface of the sleeve. An oxygen-containing gas is supplied to, and an ozone-containing gas is removed from, the channel. Additionally, the system includes a device for passing the ozone-containing gas to the conduit.

In accordance with yet another embodiment of the present invention, a system is provided for removing biofilm from, and/or for preventing biofilm from forming on, an interior surface of a conduit. The system comprises a source of an ozone-containing gas, an ultraviolet irradiator for (a) receiving source water and producing disinfected water, or (b) receiving the ozone-containing gas and producing an ozone-diminished gas, a device for selectively routing either the disinfected water or the ozone-containing gas to the conduit, and a device for selectively routing either the source water or the ozone-containing gas, downstream of the conduit, to the ultraviolet irradiator.

DETAILED DESCRIPTION OF THE INVENTION

Figure 1:
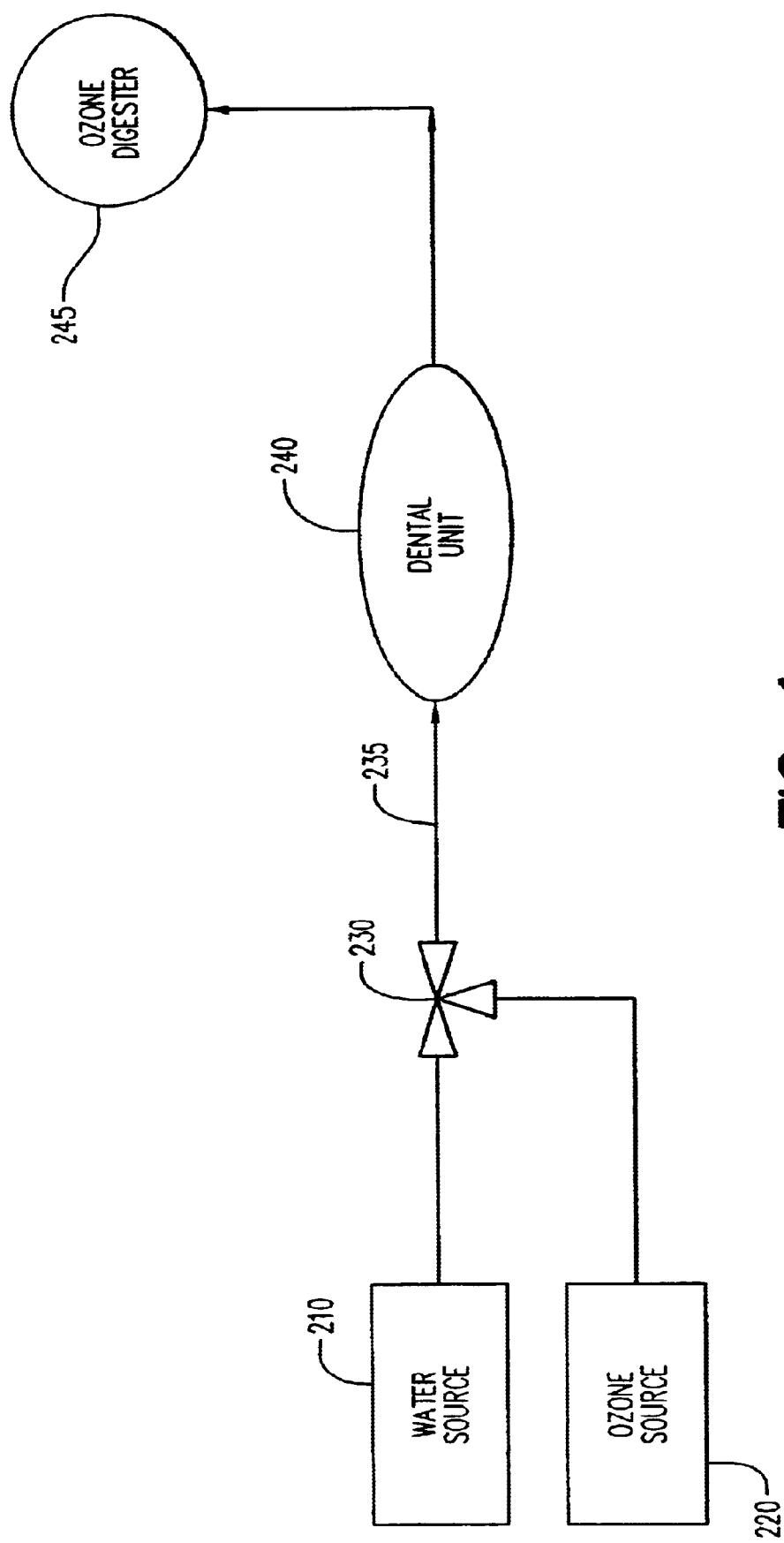
FIG. 1 is a block diagram of a system for removing biofilm from, and for preventing biofilm from forming on, an interior surface of a conduit in accordance with the present invention.

FIG. 1 is a block diagram of a system for removing biofilm from, and for preventing biofilm from forming on, an interior surface of a conduit in accordance with the present invention. The system is especially suited for use in a dental office where it can operate in conjunction with a single dental unit, or with all the equipment in the office. The system includes a water source 210, an ozone source 220, and a valve 230.

Water source 210 and ozone source 220 supply water and ozone, respectively, to valve 230. Valve 230, which may be embodied as one or more valves, selectively routes either water from water supply 210, or an ozone-containing gas from ozone supply 220, through a conduit, i.e., water line 235, to a dental unit 240. Valve 230 offers a convenient manner of selecting either the water or the ozone-containing gas.

Water source 210 can be bottled water or tap water, but more generally, the water can be supplied from any appropriate container or source. It can also be conditioned, such as by softening, or it can be sterilized or disinfected.

The ozone-containing gas, when routed through water line 235, removes biofilm from the interior surface of water line 235. By removing biofilm, the subsequent formation of biofilm is also prevented. The most effective treatment is obtained by purging water line 235 with the ozone-containing gas.

Preferably, an ozone injection occurs periodically. Controlling valve 230 automatically or semi-automatically, and having the capability of a manual override can actuate this periodic injection of ozone.

An ozone digester 245 is located downstream from dental unit 240. The ozone-containing gas is passed from dental unit 240 through ozone digester 245, which digests residual ozone. Ozone digester 245 can be a chemical or electrical device that provides this feature. For example, ozone can be destroyed by adsorption or reaction with wet granulated activated carbon, by contact with manganese dioxide, and by chemical reduction, such as by thiosulfate. Also, ultraviolet radiation with a 245 nm wavelength, the same as the germicidal frequency, can destroy ozone by converting the ozone to oxygen.

Ozone-containing gas removes biofilm much more efficiently than conventional disinfectants, such as chlorine. Also, because it is in a gaseous state, the ozone-containing gas is unlikely to leave a residual trace that can harm a user of water line 235. Ozone digester 245 further reduces the risk of harm from residual ozone.

Figure 2:
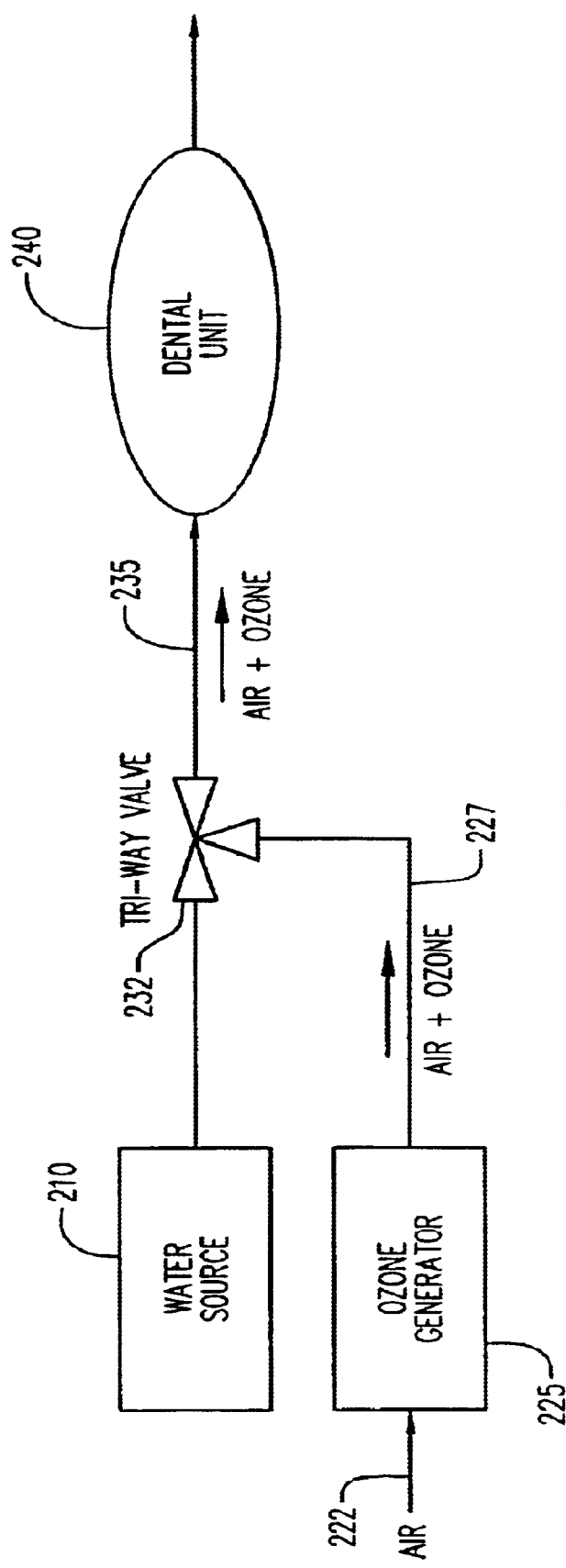
FIG. 2 is a block diagram of another embodiment of the present invention.

FIG. 2 is a block diagram of another embodiment of the present invention. In this embodiment, a tri-way valve 232 selectively routes either water from water source 210, or an ozone-containing gas from an ozone generator 225, to water line 235.

Ozone generator 225 produces an ozone-containing gas 227, for example air+ozone, from an oxygen-containing gas 222, such as air. Alternatively, the oxygen-containing gas 222 can be oxygen or oxygen-enriched air. The ozone-containing gas 227 is produced by exposing oxygen-containing gas 222 to a corona discharge or by irradiating oxygen-containing gas 222 with ultra-violet radiation.

Figure 3:
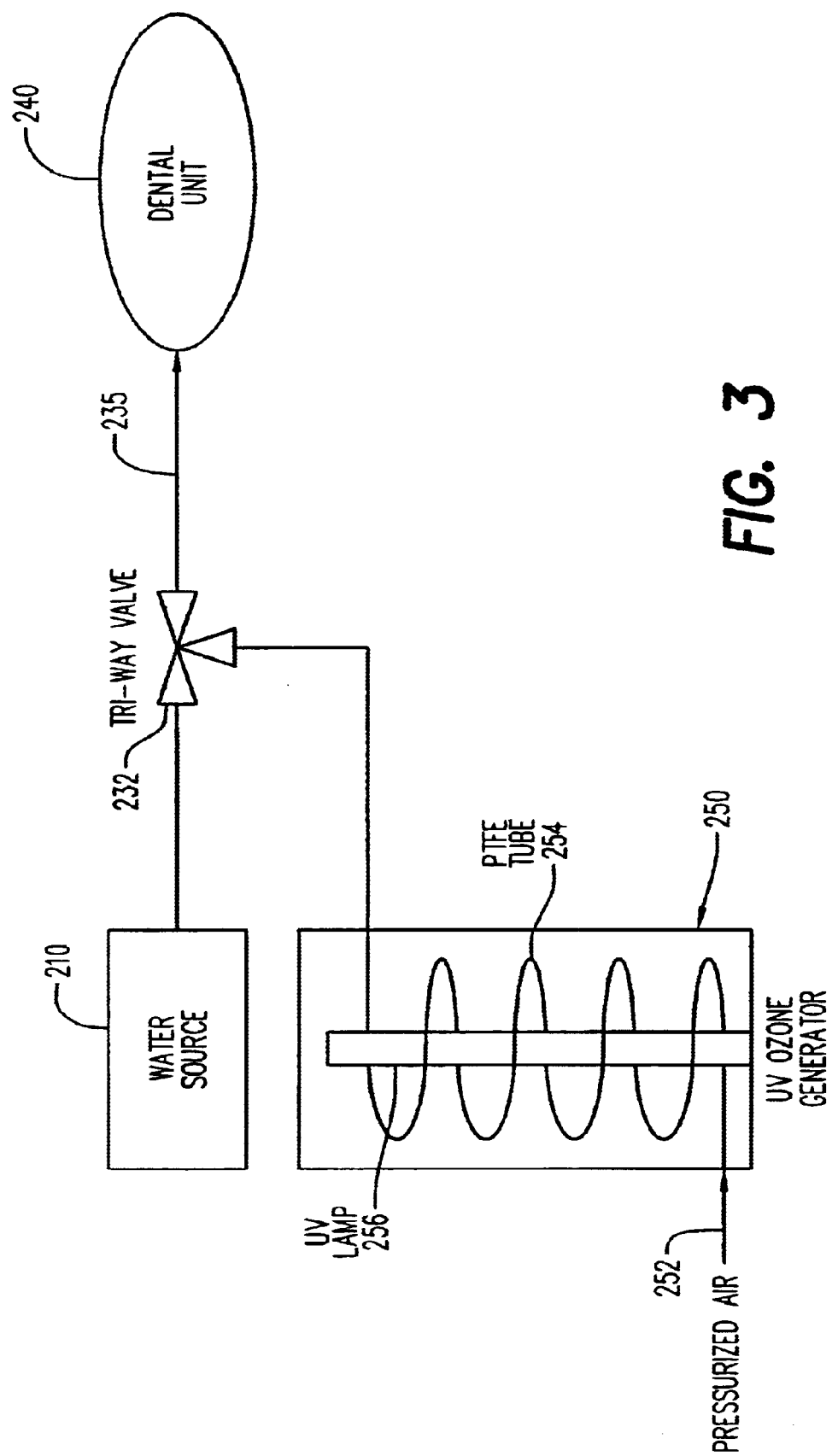
FIG. 3 is a block diagram of another embodiment of the present invention, in which an ozone generator employs the technique of irradiating an oxygen-containing gas with ultra-violet radiation.

FIG. 3 is a block diagram of another embodiment of the present invention, in which an ozone generator employs the technique of irradiating an oxygen-containing gas with ultra-violet radiation. Oxygen-containing gas 252, in this case pressurized air, is irradiated by light from an ultraviolet lamp 256. The irradiation process produces ozone-containing gas, which is routed to tri-way valve 232. The use of pressurized air enhances the purging of water line 235. Optionally, ozone generator 250 can include a tube 254, preferably made of polytetraflouroethylene (PTFE), disposed about ultraviolet lamp 256. Thus, oxygen-containing gas 252 is fed into tube 254, and ozone-containing gas is removed from tube 254.

The generation of ozone by shortwave ultraviolet radiation take place in the spectral region of 120 nm to 242 nm, with a peak output at 150 nm to 160 nm. Ultraviolet lamp 256 is preferably a 185 nm wavelength lamp. A 185 nm wavelength lamp can produce approximately 0.5 grams per hour of ozone per 425 ma of lamp current, in dry air.

Figure 4:
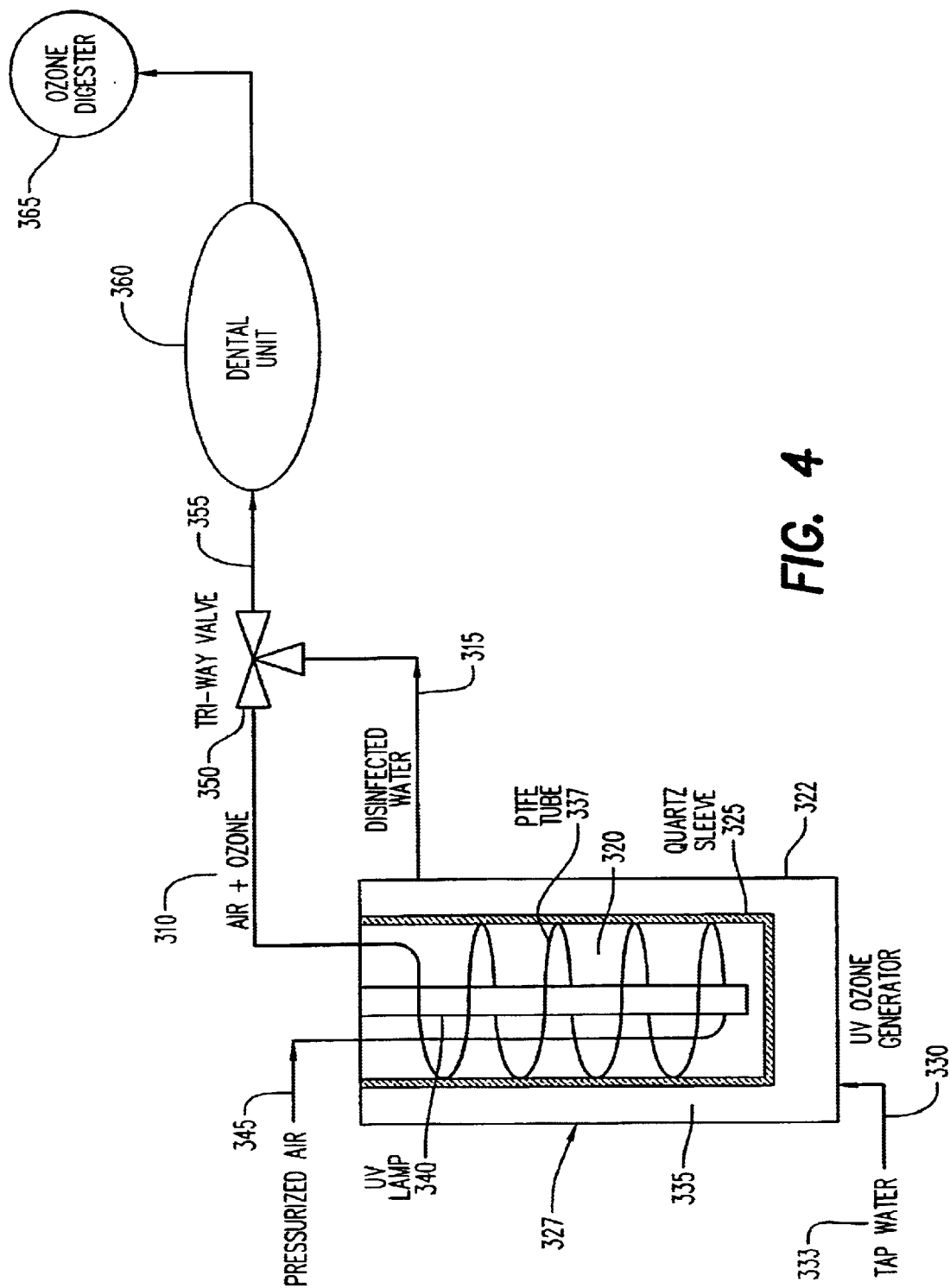
FIG. 4 is a block diagram of an embodiment of a system for removing biofilm from, and for preventing biofilm from forming on, and interior surface of a conduit, and for providing disinfected water to the conduit.

FIG. 4 is a block diagram of an embodiment of a system for removing biofilm from, and for preventing biofilm from forming on, an interior surface of a conduit. Additionally, the system provides disinfected water to the conduit. The system includes an ozone generator 327 and a tri-way valve 350.

Ozone generator 327 supplies both disinfected water 315 and ozone-containing gas 310 to tri-way valve 350. Tri-way valve 350 selectively routes either the disinfected water 315 or the ozone-containing gas 310, through a water line 355, to a dental unit 360.

The ozone-containing gas 310, when routed through water line 355, removes biofilm from the interior surface of water line 355. By removing biofilm, the subsequent formation of biofilm is also prevented. The most effective treatment is obtained by purging water line 355 with ozone-containing gas 310.

Ozone generator 327 produces ozone-containing gas 310 from an oxygen-containing gas 345, such as pressurized air. The oxygen-containing gas 345 may be air, oxygen or oxygen-enriched air, while the use of pressurized air enhances the purging of water line 355. Ozone generator 327 produces disinfected water 315 from a water supply 330, in this case tap water 333. Water supply 333 can also be bottled water, or water from any appropriate container or source, and the water can also be conditioned, such as by softening.

Ozone generator 327 includes an ultraviolet lamp 340 disposed within an ultraviolet radiation permeable sleeve 325, which may be made of quartz, hard glass, soft glass, or transparent or translucent ultraviolet resistant plastic. A channel 320 is formed between an outer surface of ultraviolet lamp 340 and an inner surface of sleeve 325. A tube 337, preferably made of PTFE, is disposed about ultraviolet lamp 340, within channel 320. An outer housing 322 surrounds sleeve 325 such that a chamber 335 is formed between the outer surface of sleeve 325 and the inner surface of housing 322.

The oxygen-containing gas 345 is supplied to tube 337 and irradiated by light from ultraviolet lamp 340. The irradiation process yields ozone-containing gas 310, which is removed from tube 337 and routed to tri-way valve 350.

The water supply 333, is fed into chamber 335 and also irradiated by light from ultraviolet lamp 340. In this case, the irradiation process yields disinfected water 315, which is removed from chamber 335 and routed to tri-way valve 350.

Ultraviolet lamp 340 is capable of producing radiation in a first wavelength range of about 120 nanometers to about 242 nanometers, preferably 185 nm, to induce the generation of a sufficient amount of ozone in the oxygen-containing gas. It is also capable of producing radiation in a second wavelength range of about 200 nanometers to about 300 nanometers, preferably 254 nm, in order to effectively kill most microorganisms such as airborne and surface bacteria, viruses, yeasts and molds. The ultraviolet lamp can be, for example, a dual wavelength low-pressure mercury lamp, or a medium pressure mercury lamp with a continuous spectrum.

An ozone digester 365 is located downstream from dental unit 360. The ozone-containing gas is passed from dental unit 360 through ozone digester 365, which digests residual ozone.

Figure 5:
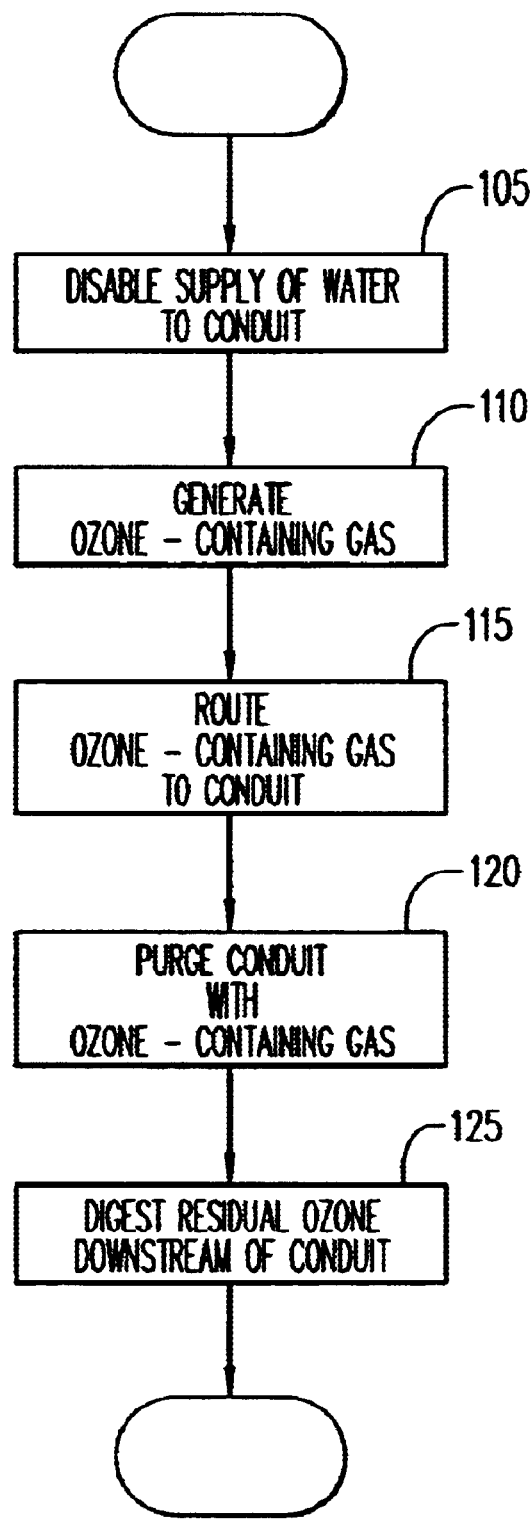
FIG. 5 is a flowchart of a method for removing biofilm from, and for preventing biofilm from forming on, an interior surface of a conduit in accordance with the present invention.

FIG. 5 is a flowchart of a method for removing biofilm from, and for preventing biofilm from forming on, an interior surface of a conduit in accordance with the present invention. Typically, the conduit is a water line, such as that used to provide a water feedstream to a dental unit.

In step 105, the supply of water to the conduit is disabled.

In step 110, an ozone-containing gas is generated.

In step 115, the ozone-containing gas is routed to the conduit.

In step 120, the conduit is purged with the ozone-containing gas.

In step 125, residual ozone is digested downstream of the conduit.

Figure 6:
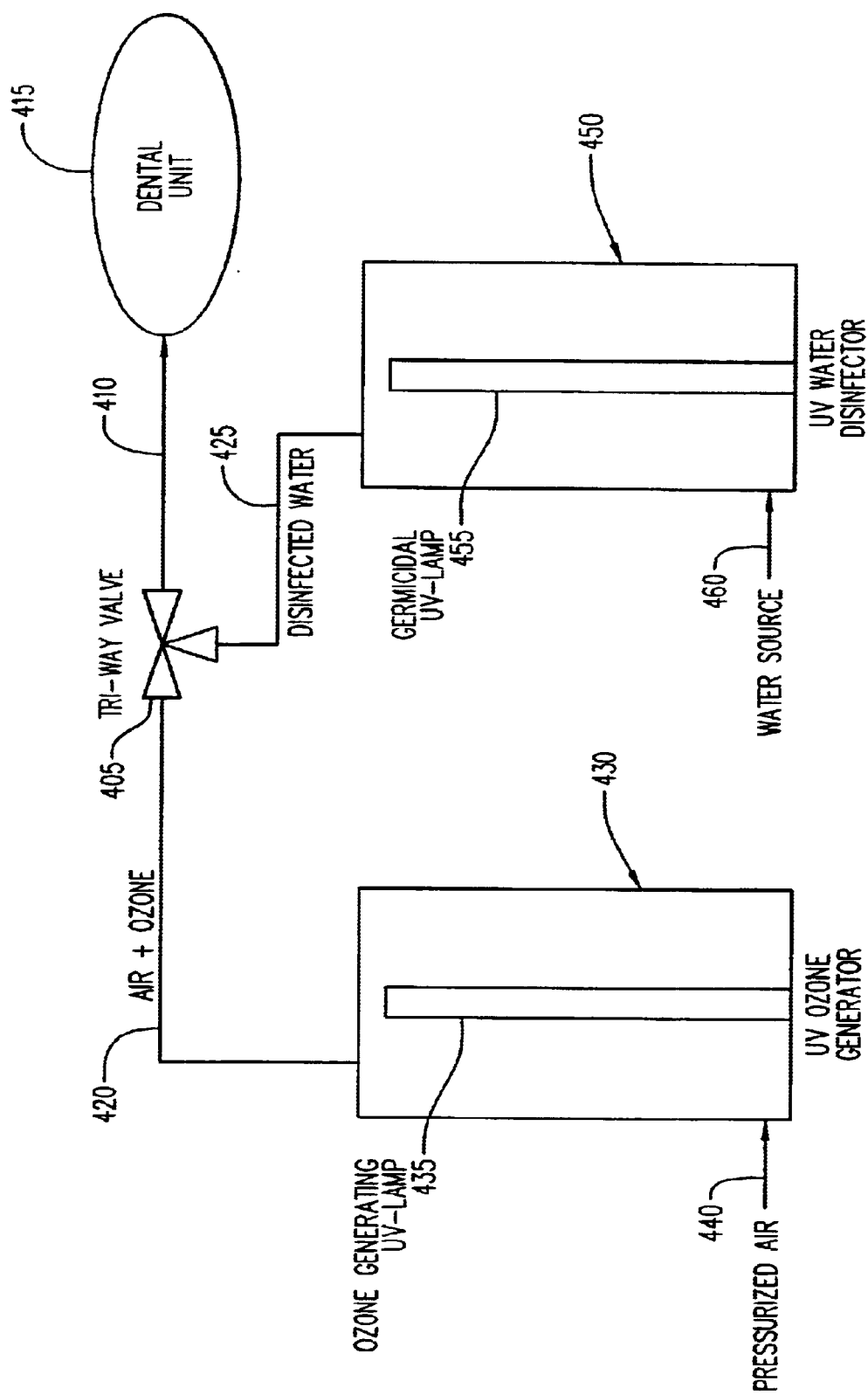
FIG. 6 is a block diagram of another embodiment of a system in accordance with the present, which includes a separate ozone generator and a separate water disinfector.

FIG. 6 is a block diagram of another embodiment of a system for removing biofilm from, and for preventing biofilm from forming on, an interior surface of a conduit, and additionally for providing disinfected water to the conduit. The system includes an ozone generator 430, a water disinfector 450 and a tri-way valve 405.

Ozone generator 430 supplies an ozone-containing gas 420 to tri-way valve 405. Water disinfector 450 supplies disinfected water 425 to tri-way valve 405. Tri-way valve 405 selectively routes either the disinfected water 425 or the ozone-containing gas 420, through a water line 410, to a dental unit 415.

Ozone generator 430 includes an ultraviolet lamp 435 for irradiating an oxygen-containing gas 440, such as pressurized air, to produce ozone-containing gas 420. The ultraviolet lamp 435 generates ultraviolet radiation with a wavelength in the range of about 120 nanometers to about 242 nanometers.

Water disinfector 450 includes an ultraviolet lamp 455 for irradiating untreated water from water source 460 to produce disinfected water 425. The ultraviolet lamp 455 generates ultraviolet radiation with a wavelength in the range of about 200 nanometers to about 300 nanometers.

Figure 7:
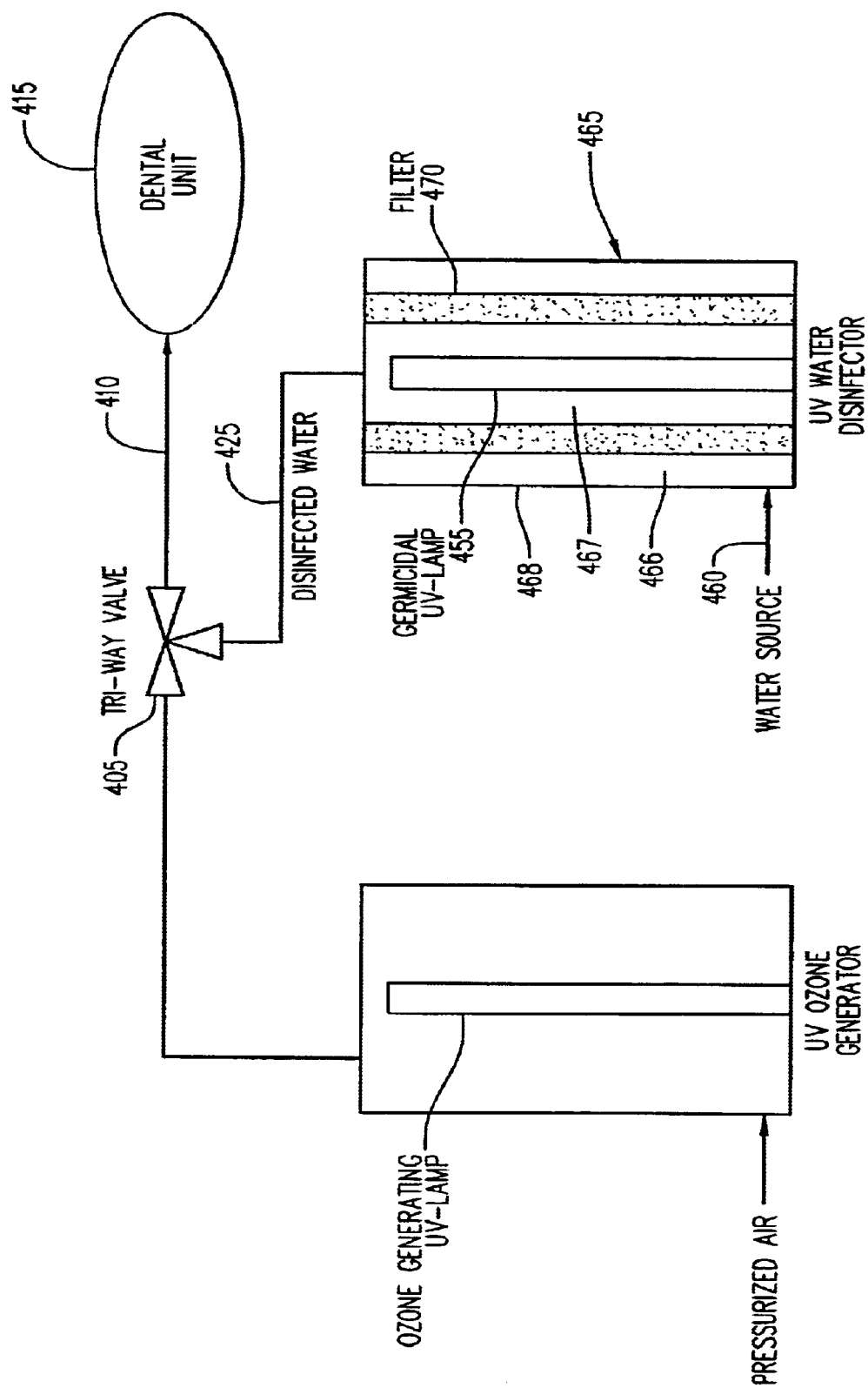
FIG. 7 is a block diagram of a system, similar to that shown in FIG. 6, in which the water disinfector includes a filtration member.

FIG. 7 is a block diagram of another system, similar to that shown in FIG. 6. Here, a water disinfector 465 also includes a filtration member 470 disposed about ultraviolet lamp 455 such that a permeate chamber 467 is formed between an outer surface of ultraviolet lamp 455 and an inner surface of filtration member 470. An outer housing 468 surrounds filtration member 470 such that a feed chamber 466 is formed between an inner surface of outer housing 468 and an outer surface of filtration member 470.

The untreated water passes from feed chamber 466 through filtration member 470 to provide a filtered water to permeate chamber 467. In permeate chamber 467, the filtered water is subjected to ultraviolet radiation generated by ultraviolet lamp 455. The filtered and radiated water is removed from permeate chamber 467 as disinfected water 425.

Filtration member 470 can be formed from at least one material selected from the group consisting of: activated carbon, activated carbon block, adsorption resins, ion exchange resins, zeolite, reduction catalysts, paper, polymers, clay, ceramics, metals, nylon, wood pulp, cellulose, cotton, fibers, and any other material capable of separating particulate, organics or inorganics from a feed stream. Filtration member 470 is preferably in the form of one of the following: string wound filter, fiber composite molded filter, pleated filter, hollow fiber membrane, spiral wound membrane or sheet, plate and frame membrane and any other conventional form.

When filtration member 470 is used to remove organic materials, such as benzene, it is preferably formed of activated carbon or adsorption resin. To remove inorganic materials, such as heavy metals, or sulfites, filtration member 470 should be formed from ion exchange resin, zeolite or a reduction catalyst. U.S. Pat. No. 5,529,689 to Korin, entitled Replaceable Integrated Water Filtration And Sterilization Cartridge And Assembly Therefor, describes an exemplary embodiment of device suitable for use as water disinfector 465.

Another exemplary embodiment of a device suitable for use as water disinfector 465 is a PURA™ UV1-EPCB water purifier from Hydrotech®, Inc. This product combines ultraviolet disinfection and carbon filtration in a compact system. The UV-1 series is rated for 1 gallon per minute flow rate and uses either a cyst rated 0.5 micron carbon block filter or a 10 micron carbon block filter.

Figure 8:
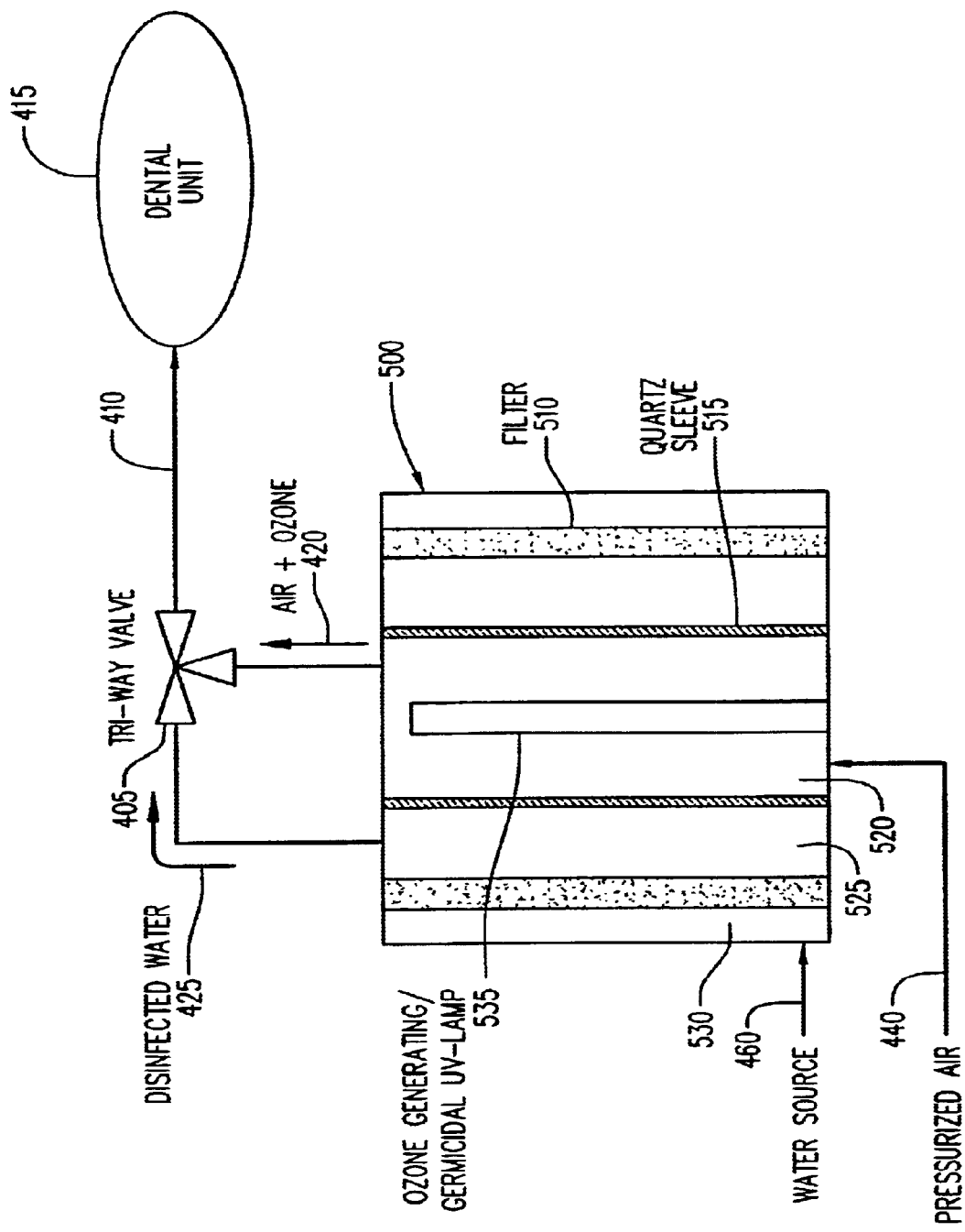
FIG. 8 is a block diagram of a system in accordance with the present invention, which includes an integrated assembly for producing disinfected water and for generating ozone-containing gas.

FIG. 8 is a block diagram of another embodiment of a system for removing and preventing biofilm, and for also providing disinfected water to a conduit. The system includes an integrated assembly 500 and a tri-way valve 405.

Integrated assembly 500 produces disinfected water 425 and generates an ozone-containing gas 420. An ultraviolet lamp 535 is disposed within an ultraviolet radiation permeable sleeve 515 such that a gas conduit 520 is formed between an outer surface of ultraviolet lamp 535 and an inner surface of sleeve 515. A filtration member 510 is disposed about sleeve 515 such that a permeate chamber 525 is formed between an outer surface of sleeve 515 and an inner surface of filtration member 510. Permeate chamber 525 is separated from gas conduit 520 such that no mixing of the water and gas occurs. A feed chamber 530 is disposed about an outer surface of filtration member 510.

Untreated water from a water source 460 is supplied to feed chamber 530 and disinfected water 425 is removed from permeate chamber 525. An oxygen-containing gas 440 is supplied to, and ozone-containing gas 420 is removed from, gas conduit 520. Tri-way valve 405 selectively routes either disinfected water 420 or ozone-containing gas 425 to conduit 410.

Ultraviolet lamp 535, in consideration of its dual role, generates ultraviolet radiation with a first wavelength in the range of about 120 nanometers to about 242 nanometers, and a second wavelength in the range of about 200 nanometers to 300 nanometers.

Figure 9:
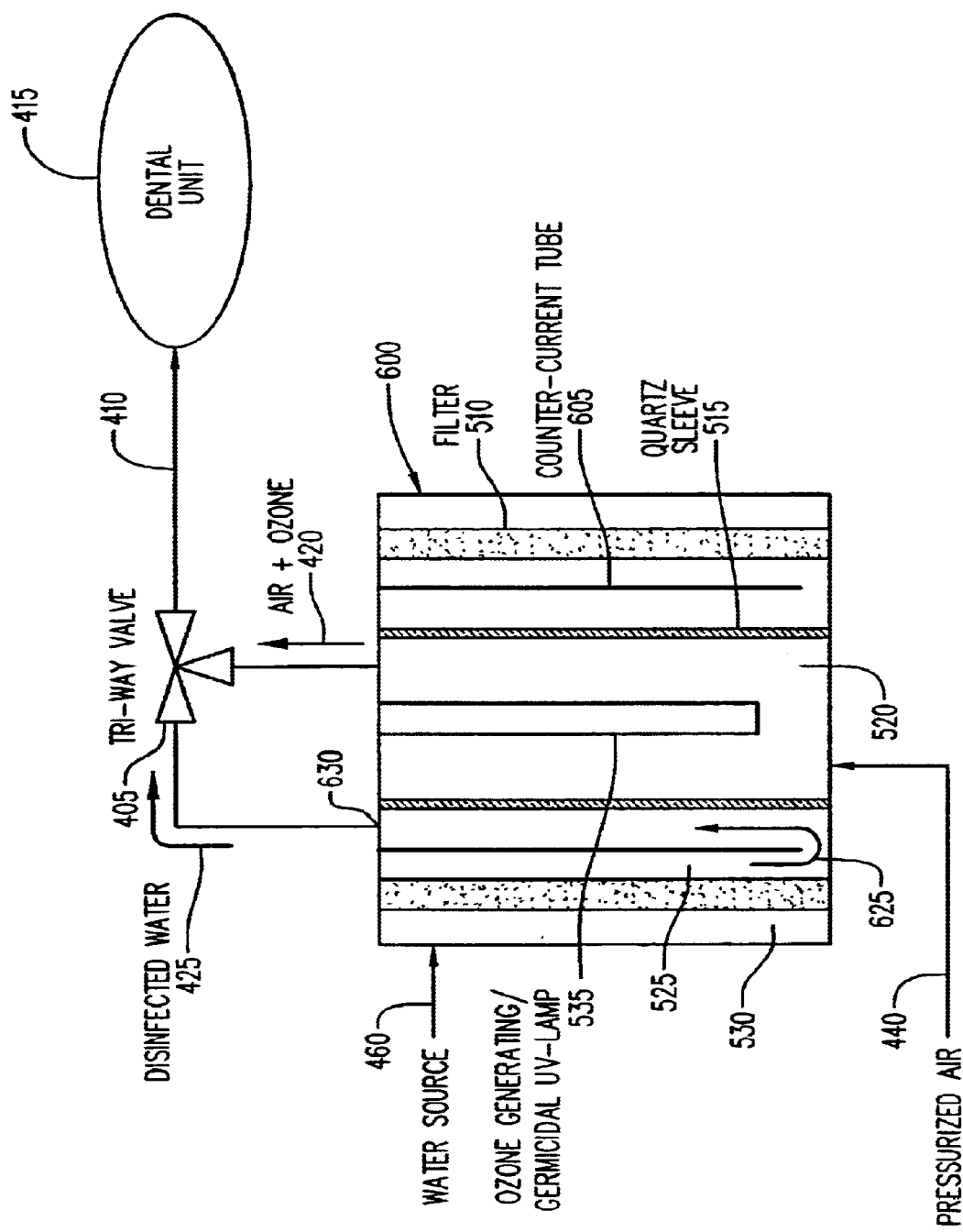
FIG. 9 is a block diagram of a system, similar to that shown in FIG. 8, in which the integrated assembly includes a counter current tube.

FIG. 9 is a block diagram of another embodiment, similar to that shown in FIG. 8. Here, an integrated assembly 600 includes a member, such as a counter-current tube 605, disposed with permeate chamber 525, for encouraging water to flow unidirectionally through permeate chamber 525. Counter-current tube 605 is positioned between an inner surface of filtration member 510, and a port 630 through which disinfected water 425 is removed from permeate chamber 525. Counter-current tube 605 interferes with a direct flow of water from filtration member 510 to port 630, by requiring the water to flow around an end of counter-current tube 605 that is most distant from port 603, illustrated here as path 625. This circuitous route increases the time during which water will be exposed to radiation from ultraviolet lamp 535, thus improving the opportunity for disinfecting the water.

Figure 10:
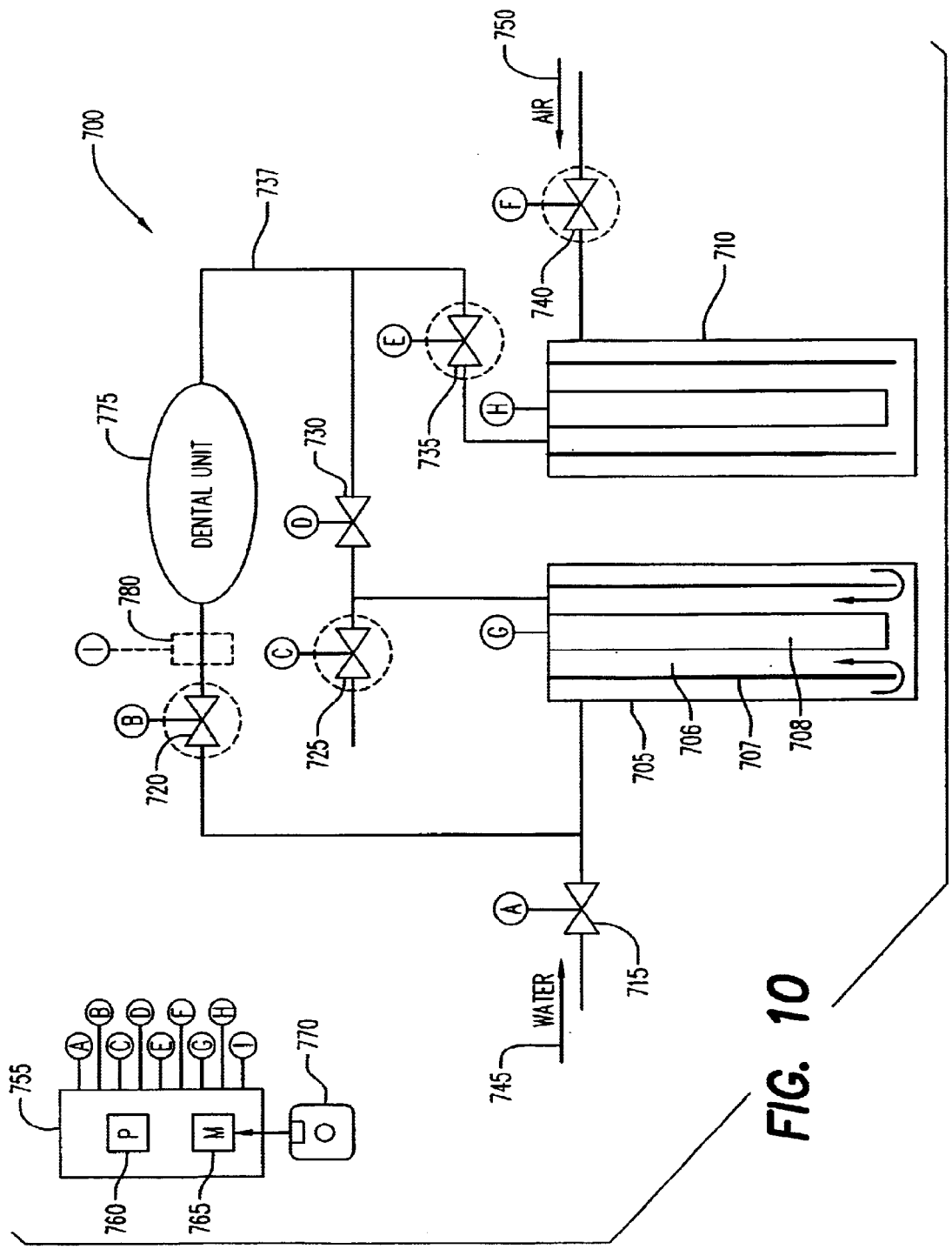
FIG. 10 is a block diagram of a system, in accordance with the present invention, configured for operation while a dental patient is being treated.
Figure 11:
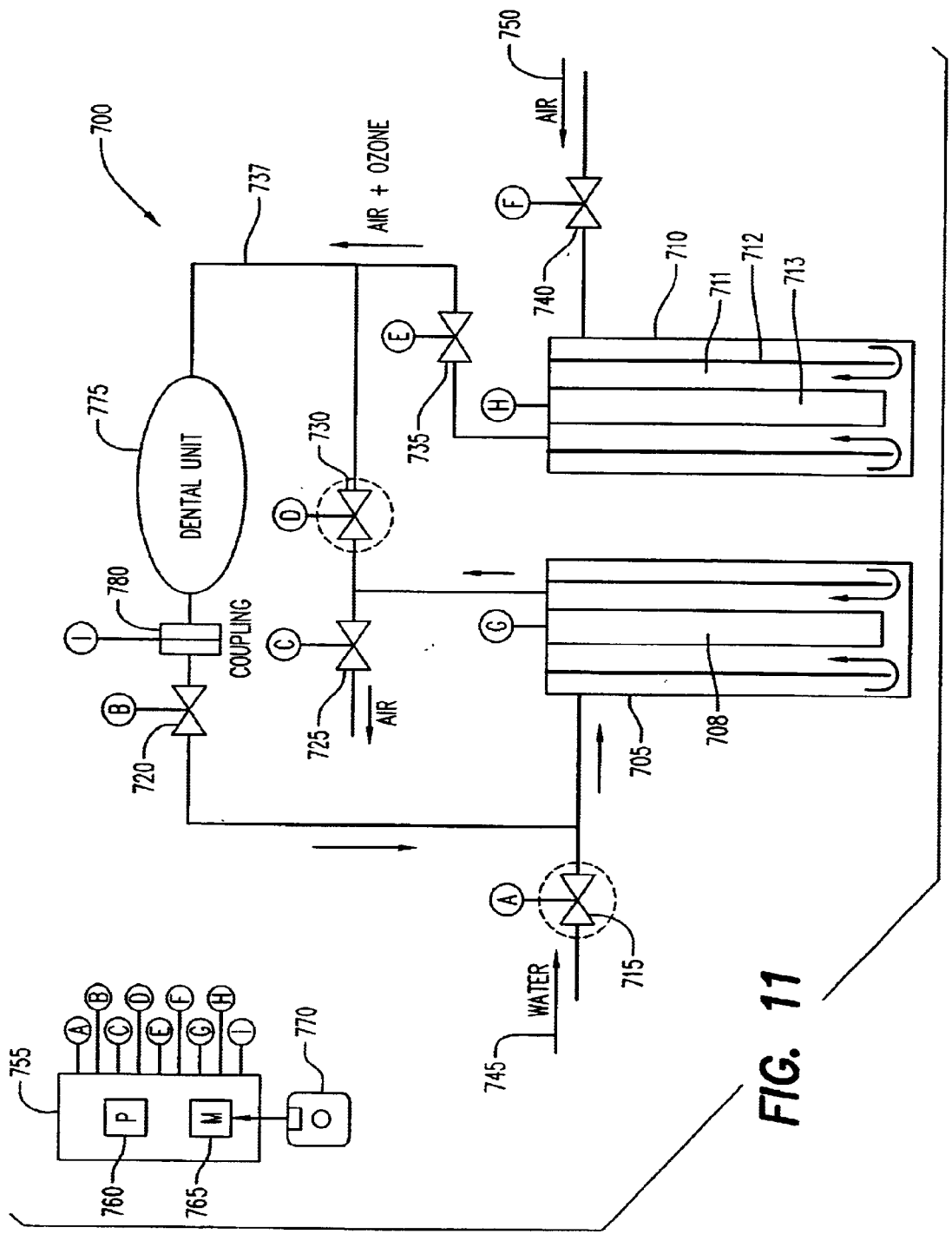
FIG. 11 is a block diagram of a system, in accordance with the present invention, configured for operation during an ozone purge cycle, while a dental patient is not being treated.

FIGS. 10 and 11 are block diagrams of a preferred embodiment of a system 700 for providing disinfected water to a dental water line, and for removing biofilm from, and for preventing biofilm from forming on, an interior surface of the dental water line. FIG. 10 depicts system 700 during business operation, that is, including times during which a dental patient it being treated. FIG. 11 depicts system 700 during non-business operation, that is, during an ozone purge cycle, while a dental patient is not being treated.

As shown in FIG. 10, system 700 includes a water disinfector 705, an ozone generator 710, and valves 715, 720, 725, 730, 735 and 740. System 700 also includes a control unit 755.

During business operation, valves 715 and 730 are opened, that is, they permit a flow of liquid or gas, and valves 720, 725, 735 and 740 are closed, that is, they inhibit the flow of liquid and gas. Water disinfector 705 includes a germicidal UV lamp 708, which is turned on. Water 745 enters system 700 via valve 715 and flows into water disinfector 705. Inside of water disinfector 705, the water flows parallel to a length of lamp 708, through a chamber 706 formed between an outer surface of lamp 708 and an inner surface of a UV resistant tube 707. Disinfected water exits water disinfector 705, flows through valve 730, through a dental water line 737, and into a dental unit 775. Use of water disinfector 705 enables a use of tap water as a source of water 745.

Referring to FIG. 11, during non-business operation, valves 715 and 730 are closed, and valves 720, 725, 735 and 740 are opened. Ozone generator 710 includes an ozone-generating lamp 713, which is turned on and emits UV light including a wavelength of 185 nm. Air 740 enters system 700 via valve 740 and flows into ozone generator 710. Inside of ozone generator 710, the air flows parallel to a length of lamp 713, through a chamber 711 formed between an outer surface of lamp 713 and an inner surface of a UV resistant tube 712. Ozone enriched air exits ozone generator 710, flows through valve 735, through dental water line 737 and into dental unit 775. The ozone-enriched air purges dental water line 737 and destroys bacterial biofilm that may be present therein.

The ozone-enriched air exists dental unit 775 via a coupling 780, and is routed through valve 720 and into water disinfector 705. Lamp 708, which is on, emits UV light including a wavelength of 254 nm. The ozone-enriched air passes around lamp 708 and the ozone is destroyed by the 254 nm UV. Ozone-diminished air exits disinfector 705, and it is routed through valve 725 and vented out of system 700. Optionally, to prevent a release of any residual ozone from system 700, the output of valve 725 can be directed to a filter (not shown) that destroys ozone by adsorption or reaction with wet granulated activated carbon, by contact with manganese dioxide, or by chemical reduction, such as by thiosulfate.

The operation of valves 715, 720, 725, 730, 735 and 740 can be automated, when they are, for example, of a solenoid or pneumatic configuration. Coupling 780 may also be of a solenoid or pneumatic configuration, in which case its operation can be automated, or it may be a quick disconnect coupling, similar to a dental hand piece coupling, in which case it is manually installed and removed.

Control unit 755 controls the automation of system 700. More particularly, control unit 755 controls the actuation of valves 715, 720, 725, 730, 735 and 740, the switching of lamps 708 and 713, and a timing of a purge cycle during non-business operation of system 700. Accordingly, control unit 755 provides a control signal to each of the components that it controls. The control signals are represented in FIGS. 10 and 11 as being routed via connections A through I.

In its preferred embodiment, control unit 755 is a conventional computer or a programmable controller. Accordingly, control unit 755 includes a processor 760, and a memory 765 that contains data and instructions, typically in the form of executable program code. Processor 760 can be any conventional microprocessor or other programmable device. The instructions contained within memory 765 control processor 760 to disable the supply of water to dental water line 737, and instead, to route the ozone-enriched air to water line 737.

While the procedures required to execute the invention hereof are indicated as already loaded into memory 765, they may be configured on a storage media 770, for subsequent loading into memory 765. Storage media 770 may be any conventional data storage device such as, but not limited to, a magnetic disk, a magnetic tape, a read only memory, a random access memory, a hard disk or a floppy disk, or an optical storage media.

Restricting the flow of the ozone-enriched air through water line 737 even further enhances the removal of biofilm from dental water line 737. For example, assuming that the ozone-enriched air flows through an orifice within coupling 780, controlling the diameter of the orifice can control the restriction. The smaller the diameter, the greater the restriction. The restriction provides a back-pressure on dental water line 737 that reduces the rate at which the ozone-enriched air passes therethrough, thus enabling the ozone-enriched air to remain in dental water line 737 for a longer period of time.

Optionally, the removal of biofilm from dental water line 737 can be enhanced by periodically flushing it with a disinfectant, such as hypochlorite, chlorine dioxide ($ClO_2$) solution, hydrogen peroxide or other type of commercial disinfectant, such as BioVAC™ from Micrylium Labs™. Ideally, the disinfectant flush is performed either monthly or every other month. The disinfectant solution may be introduced by means of a siphoned bottle (not shown) coupled to water line 737 by a tee fitting (not shown) and a check valve (not shown), and the use of pressurized air as a driving force.

The efficacy of purging a system with ozone-enriched air was evaluated in a series of tests performed using an in vitro water system simulation device. The in vitro dental water system simulation device was essentially made up of materials and equipment that used in dental units (ADEC). The design (scale and function) of the system simulated real dental unit water systems (4 hand piece lines, 1 air/water syringe) per group and the unit consisted of 8 such groups. The system could access 4 different sources of water and was controlled by a computer that controlled the air solenoids to run this automated system.

In this study 4 clean units (biofilm and microbe free lines) were used. Each of the units was standardized based on frequency and flow rate (600 ml/day for a period of 6 hours per day). Prior to beginning of this study a six week observational study was done using 4 units of the system. Two units used tap water and two used sterile deionized water. One unit each in the tap water and the sterile water groups was free of biofilms while the other had existing naturally grown biofilms. Heterotrophic plate counts in units of cells per milliliter (CFU/ml) were taken at baseline and once weekly using R2A agar. The results of the heterotrophic plate count measurements are presented in Table 1.

TABLE 1

HETEROTROPHIC PLATE COUNTS (CFU/ml)

| Sample ID | Tap Water | Sterile Water | Tap Water & No Biofilm | Tap Water & Biofilm Present | Sterile Water & No Biofilm | Sterile Water & Biofilm Present |
|---|---|---|---|---|---|---|
| Baseline | 40 | 0 | 10 | >400,000 | 10 | >400,000 |
| Week 1 | 60 | 0 | >400 | >400,000 | 360 | >400,000 |
| Week 2 | 270 | 0 | 2,800 | >400,000 | >4,000 | >400,000 |
| Week 3 | 10 | 0 | >4,000 | >400,000 | >4,000 | >400,000 |
| Week 4 | 70 | 0 | >32,000 | >400,000 | >18,000 | >400,000 |
| Week 5 | >400 | 0 | >40,000 | >400,000 | >40,000 | >400,000 |
| Week 6 | 20 | 0 | >40,000 | >400,000 | >40,000 | >400,000 |

Taking for example the unit that used tap water and had no biofilm present at the beginning of the study, Table 1 shows that the unit had a baseline measurement of 10 CFU/ml, and after week 6, >40,000 CFU/ml. Note also that in the unit that used sterile water and had no biofilm present at the beginning of the study, after week 6, the unit also had >40,000 CFU/ml. This six week observational study shows that even with sterile water, a system may eventually become contaminated with biofilm.

After the six-week observational study, four groups of systems were studied to evaluate their ability to control biofilms and planktonic contamination. The groups were configured as described below.

Experimental Groups

Group 1 (G1): Lines are free of biofilm at the beginning of the study.
  One unit with 4 handpiece lines and one air/water syringe line (with an air/water syringe).
  Source water is filtered-UV disinfected water derived from a UV/filter cartridge.
  Cleaning involved purging the lines once weekly for 4 weeks and then once daily for the remainder of the study with ozonated air.

Group 2 (G2): Mature biofilm present in the lines at the beginning of the study.
  One unit with 4 handpiece lines and one air/water syringe line (with an air/water syringe).
  Source water is filtered-UV disinfected water.
  Cleaning involved purging lines for one 10-minute session at the end of each workday with ozonated air.

Group 3 (G3): Mature biofilm present in the lines at the beginning of the study.
  One unit with 4 handpiece lines and one air/water syringe line (with an air/water syringe).
  Source water is filtered-UV disinfected water.
  Cleaning involved purging lines for 20-minute sessions at the end of each workday with ozonated air.

Group 4 (G4): Lines free of biofilm at the beginning of the study.
  One unit with 4 Handpiece lines and one air/water syringe line (with an air/water syringe).
  Source Water is Filtered-UV disinfected water.
  Cleaning involved purging lines for a 20-minute session at the end of each week with ozonated air for the first 4 weeks and then daily for the remainder of the study.

After 4 weeks, all groups were purged with 200 ppm of $ClO_2$ for about 2.5 minutes on a monthly basis for additional control. Additionally, an 0.2 mm orifice was placed at the outlet of each of the four lines to restrict the flow of the ozone-containing air, thus increasing the back-pressure during the purging cycles.

Study Period
Phase 1: 1 week
Phase 2: 12 weeks

Heterotrophic Plate Counts

Phase 1: Baseline and one beginning of day source water (tap/sterile) and effluent water collected (20 ml) for 4 consecutive days, plated on buffered R2A agar using standard microbiological methods, incubated at 22 to 24 degrees Celsius for a period of 7 days and counted using a Quebec Counter.

Phase 2: One beginning of week source water (tap/sterile) and effluent water were collected (20 ml) for 12 consecutive weeks, plated on buffered R2A agar using standard microbiological methods, incubated at 22 to 24 degrees Celsius for a period of 7 days and counted using a Quebec Counter.

Table 2 lists the heterotrophic plate counts of the effluent water from each group. In all four groups, the purge was applied under back-pressure in weeks 5 through 10.

G1: No biofilm at beginning.
  Ozone purge: Weeks 1–4, 10 min/week;
  Weeks 5+, 10 min/day.

G2: Mature biofilm at beginning.
  Ozone purge, 10 min/day.

G3: Mature biofilm at beginning.
  Ozone purge, 20 min/day.

G4: No biofilm at beginning.
  Ozone purge: Weeks 1–4, 20 min/week;
  Weeks 5+, 20 min/day

TABLE 2

HETEROTROPHIC PLATE COUNTS (CFU/ml)

| Sample | Tap | G1 | G2 | G3 | G4 |
|---|---|---|---|---|---|
| Baseline | 400 | 0 | >400,000 | >400,000 | 0 |
| Day 1 | 100 | 10 | >40,000 | >4,000 | 780 |
| Day 2 | 60 | 40 | >4,000 | >4,000 | >4,000 |
| Day 3 | 400 | >400 | >4,000 | 900 | >4,000 |
| Day 4 | 1200 | >4,000 | >4,000 | 700 | >4,000 |
| Week 2 | 600 | >4,000 | >4,000 | 800 | >4,000 |
| Week 3 | 20 | >40,000 | >4,000 | 140 | >4,000 |
| Week 4 | 70 | >40,000 | >4,000 | 210 | >4,000 |
| Change In Protocol where after week 4 in the study: G1 and G2 daily 10 min ozone purge; G3 and G4 daily 20 min ozone purge. For all four groups, the outlet water line was restricted with a 0.2 mm orifice to increase the ozone back-pressure within the line. | | | | | |
| Groups 1, 2, 3 and 4 cleaned with 200 ppm $ClO_2$ (2.5 minutes flush) | | | | | |
| Week 5 | 600 | 20 | 60 | 0 | 50 |
| Week 6 | 180 | 140 | 20 | 40 | 10 |
| Week 7 | 380 | 60 | 220 | 10 | 310 |
| Week 8 | 10 | 10 | 80 | 170 | 40 |
| Groups 1, 2, 3, 4 cleaned with 200 ppm of $ClO_2$ (2.5 minutes flush) | | | | | |
| Week 9 | 50 | 100 | 10 | 110 | 230 |
| Week 10 | 90 | 110 | 240 | 20 | 460 |
| Week 11 | 40 | 210 | 130 | 370 | 330 |
| Week 12 | 920 | 180 | 220 | 90 | 300 |

Figure 12:
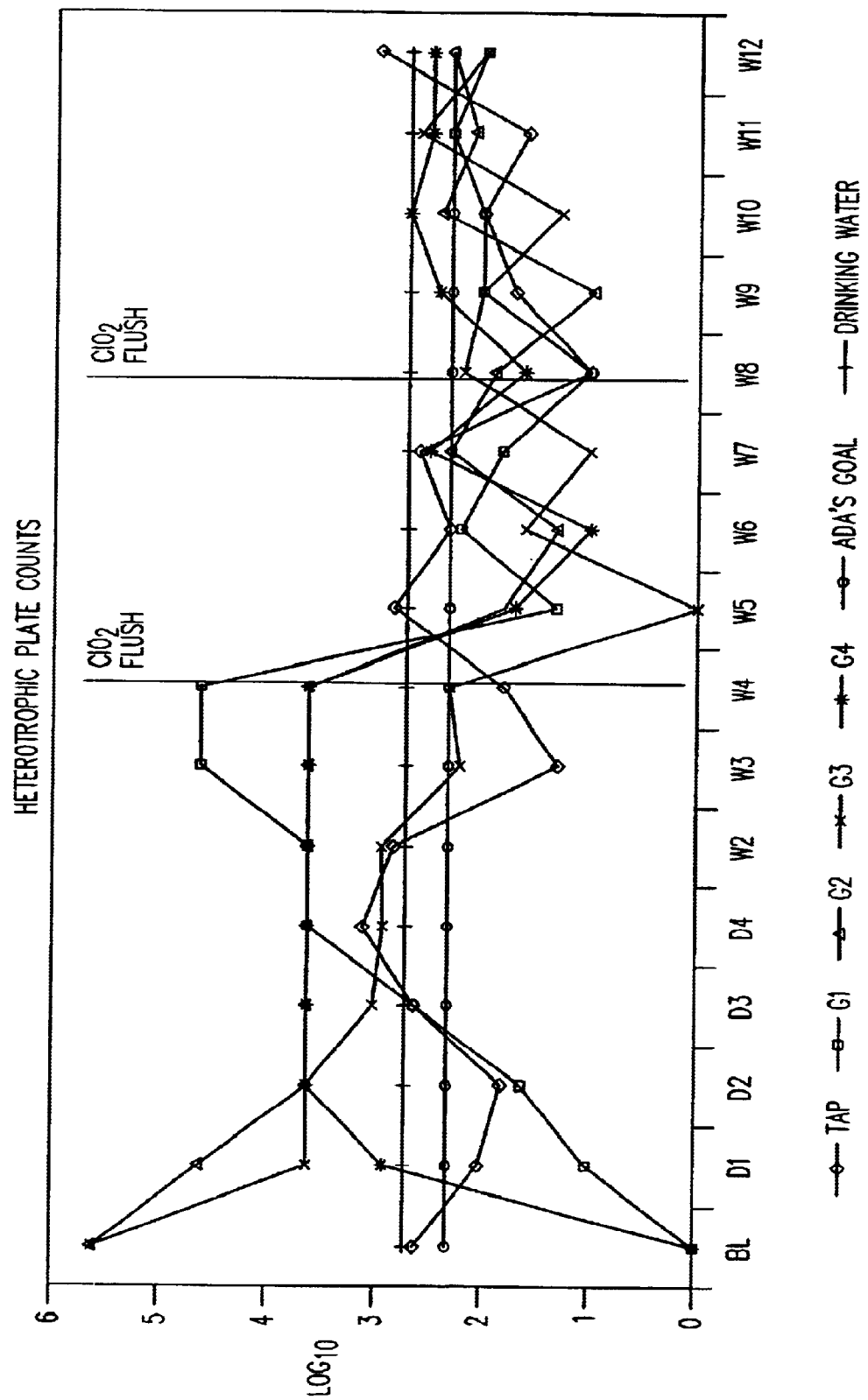
FIG. 12 is a graph of heterotrophic plate counts taken during a 12 week evaluation of the efficacy of a system in accordance with the present invention.

FIG. 12 is a graph of the heterotrophic plate count data represented in Table 2.

During the first four weeks G1, which began with clean lines, became contaminated to over 40,000 CFU/ml. G2, which began with biofilm contamination in excess of 400,000 CFU/ml, showed a reduction to about 4,000 CFU/ml. G3, at the beginning had mature biofilm and contamination levels in excess of 400,000 CFU/ml, but by the end of day 3 in the first phase, with 20 minutes/day of purging with ozone gas, the colony forming units were reduced to <1,000 and remained so until the end of the study. G4 had no biofilm to begin with but was purged with ozonated air once weekly. By the end of the second day, the contamination levels rose to >4,000 CFU/ml and remained so till the end of the $4^{th}$ week.

These results show that if there is no treatment with ozone-enriched air, the effluent water contamination levels increase both in lines that were clean and biofilm-free to begin with, and in lines that began with biofilm contamination. Previous studies on the same automated experimental device showed no difference in the contamination levels in control groups, over time, regarding biofilms or heterotrophic plate counts. Therefore in such experiments, it is redundant to have control groups that show consistent presence of contamination over the experimental time. These results demonstrate that preferably, a system should be purged with ozonated air for at least 20 minutes per day for controlling biofilm and subsequent dental treatment water contamination.

These results also show that lines G2 and G4, which were purged under free flow conditions, showed biofilm control results, but both stabilized at a level of 400 CFU/ml, which is an order of magnitude greater than an American Dental Association target level of 200 CFU/ml. G1 and G3 showed that a weekly purge is not sufficient for biofilm control.

All four groups were provided with filtered UV-disinfected water of <200 CFU/ml. After the 4$^{th}$ week, all groups were cleaned with about 200 ppm of $ClO_2$ (clorine dioxide) for about 2.5 minutes, and thereafter, the cleaning process was repeated monthly. The outlet of each water line was restricted with a 0.2 mm orifice to increase the ozone back-pressure within the lines. For the remaining 8 weeks, all groups showed contamination <400 CFU/ml with values reaching even less than 10 CFU/ml. FIG. 12 shows that most of the results yielded populations approximating the desired level of 200 CFU/ml, as recommended by the American Dental Association. Further optimization of operating conditions may yield even lower levels of bacteria in water, and improved biofilm control.

These results are better than conventional standards for contamination levels of drinking water leaving municipal water treatment plants, and they are considered safe. Although the American Dental Association (ADA) set a goal of 200 CFU/ml for the year 2000, there is no significant evidence of any risk with water being of potable quality for use in dental care.

On the other hand, tap water was found to have inconsistent levels of contamination, both microbiologically and with respect to TDS. Tap water is not appropriate for use during dental treatment as the contamination levels ranged from 10 CFU/ml to 1,200 CFU/ml and was higher than that of the effluent from the hand piece and air/water syringe lines of the 4 treatment groups. Although the present invention encompasses a system for the prevention of biofilm growth that uses tap water as a water source, such as that shown in FIG. 1, an integrated system such as one of those shown in FIGS. 10 or 11 is preferred to avoid the effect of contamination from tap water. During the complete period of this study none of the groups showed any visible corrosion or material breakdown due to ozonation.

Table 3 reports the outcome of scanning electron microscopy (SEM) for the four groups.

TABLE 3

OUTCOMES OF SCANNING ELECTRO MICROSCOPY (1500X)

| Criteria | Baseline | | | | Post Study | | | |
| --- | --- | --- | --- | --- | --- | --- | --- | --- |
| | G1 | G2 | G3 | G4 | G1 | G2 | G3 | G4 |
| Mature biolfilm matrix + visible bacteria | | X | X | | | | | |
| Biofilm without matrix + visible bacteria | | | | | | | | |
| Presence of visible bacteria but no biofilm | | | | | X | X | X | X |
| No biofilm and bacteria present | X | | | X | | | | |

At the baseline, G1 and G4 had no biofilms, whereas the remaining two groups, G2 and G3, had mature biofilms with a matrix interspersed with visible microorganisms. By the end of the study all groups showed no biofilm matrix, but for only scattered microorganisms on the lumenal surface of the waterlines.

Figure 13:
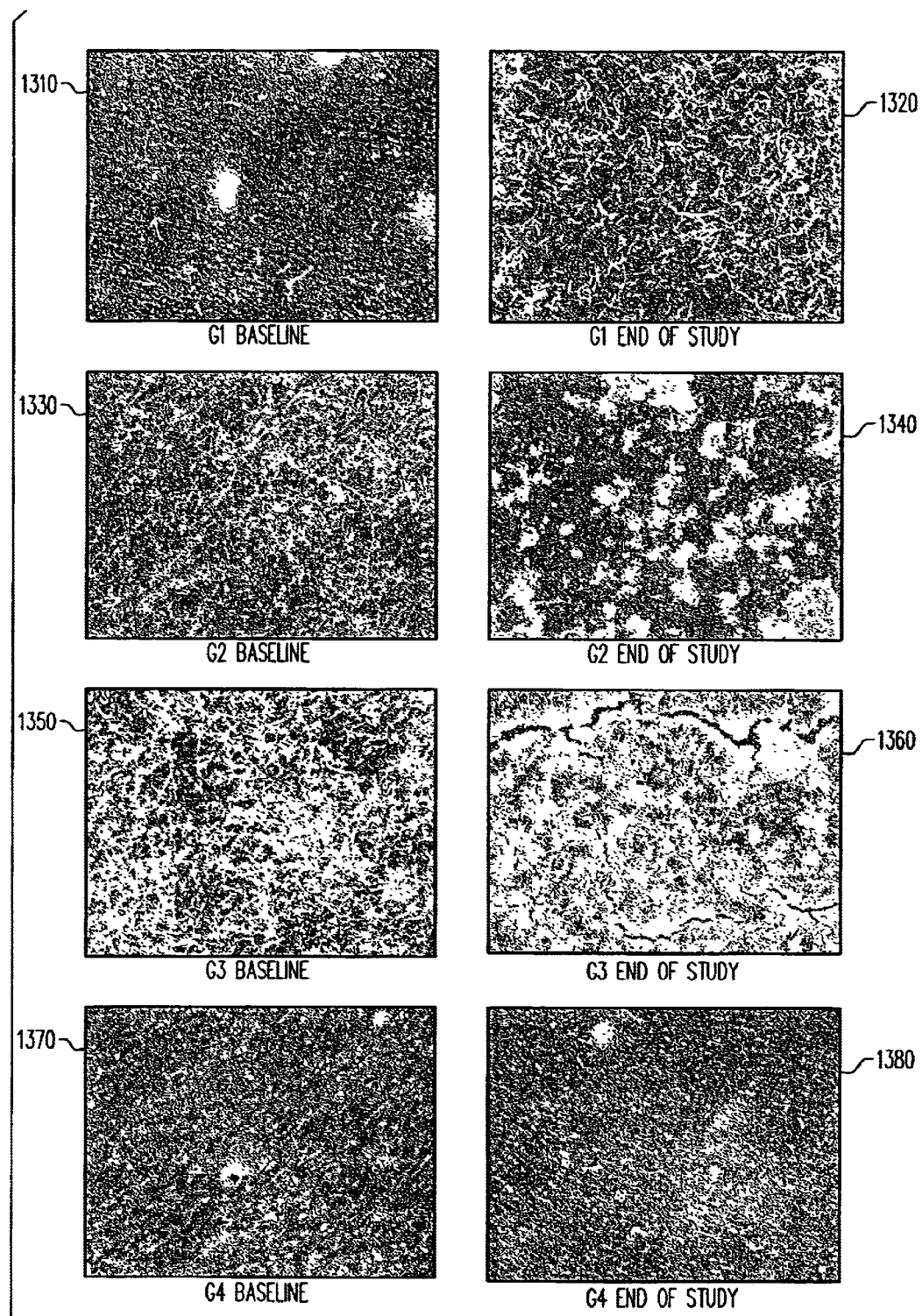
FIG. 13 shows images of biofilm cultures from waterlines at the beginning of a study and at the end of the study, taken by an SEM.

FIG. 13 shows images of samples from each of the groups, at the beginning of the study and at the end of the study, taken by an SEM.

G1 baseline image 1310 shows that at the beginning of the study the line was clean and had no biofilm.

G1 end of study image 1320 shows that at the end of the study the line remained free of mature biofilm matrix. There are some scattered microbes without a mature matrix.

G2 baseline image 1330 shows that at the beginning of the study the line had mature biofilm.

G2 end of study image 1340 shows that at the end of the study the line had some scattered microbes without a mature matrix.

G3 baseline image 1350 shows that at the beginning of the study the line had mature biofilm.

G3 end of study image 1360 shows that at the end of the study the line had some scattered microbes without a mature matrix. The line also included inorganic pavementing, with a possible accumulation of calcium and magnesium salts, which are commonly found deposited in lines fed with hard water.

G4 baseline image 1370 shows that at the beginning of the study the line was clean and had no biofilm.

G4 end of study image 1380 shows that at the end of the study the line was clean and free of biofilm.

In conclusion, ozonation of a dental unit water system is an effective method for controlling biofilm in the system, especially if the introduction of ozone is automated. Regular ozonation of the waterlines with periodic (monthly) purging with a low grade $ClO_2$ is very efficacious in providing dental treatment water as well as controlling waterline biofilms.

Those skilled in the art, having the benefit of the teachings of the present invention may impart numerous modifications thereto. Such modifications are to be construed as lying within the scope of the present invention, as defined by the appended claims.

I claim:

1. A method for removing biofilm from, and/or for preventing biofilm from forming on, an interior surface of a conduit that receives a supply of water, comprising:

disabling said supply of water to said conduit; and passing an ozone-containing gas through said conduit.

2. The method of claim 1, further comprising, before said disabling step, disinfecting said supply of water.

3. The method of claim 2, wherein said disinfecting step comprises irradiating said supply of water with ultraviolet radiation.

4. The method of claim 3, wherein said ultraviolet radiation includes a wavelength in the range of about 200 nanometers to about 300 nanometers.

5. The method of claim 1, wherein said ozone-containing gas is pressurized.

6. The method of claim 1, further comprising generating said ozone-containing gas from an oxygen-containing gas, wherein said oxygen-containing gas is at least one selected from the group consisting of:

air, oxygen and oxygen-enriched air.

7. The method of claim 6, wherein said generating step comprises exposing said oxygen-containing gas to a corona discharge.

8. The method of claim 6, wherein said generating step comprises irradiating said oxygen-containing gas with ultraviolet radiation.

9. The method of claim 8, wherein said ultraviolet radiation includes a wavelength in the range of about 120 nanometers to about 242 nanometers.

10. The method of claim 8, wherein said irradiating step comprises:

feeding said oxygen-containing gas to a tube disposed about an ultraviolet lamp; and removing said ozone-containing gas from said tube.

11. The method of claim 1, further comprising digesting residual ozone downstream of said conduit.

12. The method of claim 11, wherein said digesting step comprises at least one technique selected from the group consisting of: (a) adsorption, (b) reaction with carbon, (c) contact with manganese dioxide, (d) chemical reduction by thiosulfate, and (e) irradiation with light including a wavelength between 200 nanometers and 300 nanometers.

13. The method of claim 1, further comprising, after said disabling step, flushing said conduit with a disinfectant.

14. The method of claim 13, wherein said disinfectant is at least one selected from the group consisting of: hypochlorite, chlorine dioxide ($ClO_2$) solution, and hydrogen peroxide.

15. The method of claim 1, further comprising restricting a flow of said ozone-containing gas downstream of said conduit.

16. A method of claim 1, wherein said conduit is a dental water line.

* * * * *